United States Patent
Saliger

(10) Patent No.: US 10,076,388 B2
(45) Date of Patent: Sep. 18, 2018

(54) METHOD AND DEVICE FOR THE PRODUCTION OF A DENTAL PROSTHESIS PART

(71) Applicant: Sirona Dental Systems GmbH, Bensheim (DE)

(72) Inventor: Günter Saliger, Bensheim (DE)

(73) Assignee: Sirona Dental Systems GMBH, Benshiem (DE)

( * ) Notice: Subject to any disclaimer, the term of this patent is extended or adjusted under 35 U.S.C. 154(b) by 893 days.

(21) Appl. No.: 14/189,441

(22) Filed: Feb. 25, 2014

(65) Prior Publication Data
US 2014/0255875 A1 Sep. 11, 2014

(30) Foreign Application Priority Data
Mar. 5, 2013 (DE) .................... 10 2013 203 750

(51) Int. Cl.
*A61C 13/00* (2006.01)
*A61C 13/08* (2006.01)
(Continued)

(52) U.S. Cl.
CPC ............ *A61C 13/0004* (2013.01); *A61C 5/70* (2017.02); *A61C 9/004* (2013.01); *A61C 13/0022* (2013.01); *A61C 13/082* (2013.01)

(58) Field of Classification Search
CPC ....... A61C 5/08; A61C 9/004; A61C 13/0004; A61C 13/0022; A61C 13/082
(Continued)

(56) References Cited

U.S. PATENT DOCUMENTS 4,970,032 A * 11/1990 Rotsaert ............. A61C 13/0003
                                                        264/139
5,151,044 A    9/1992 Rotsaert ........................ 433/229
(Continued)

FOREIGN PATENT DOCUMENTS

DE       690 01 439 T2     7/1993
DE       196 54 055 A1    12/1996
(Continued)

OTHER PUBLICATIONS

German Patent Office, Office Action dated Oct. 9, 2013, issued in connection with German Application No. 10 2013 203 750.3, 5 pages, with translation.
(Continued)

*Primary Examiner* — Ryan D. Coyer
(74) *Attorney, Agent, or Firm* — Fitzpatrick, Cella, Harper & Scinto

(57) ABSTRACT

The method for the production of a dental prosthesis part comprises the provision (11) of a dataset (2) for a dental prosthesis part (6) for use in a CAD/CAM technique, the provision (12) of reference data (3) for optical properties of different dentin materials and translucent enamel materials for the dental prosthesis part (6) and a relationship (4) between said optical properties, the desired optical properties and the dimensions of the dental prosthesis part (6), the definition (13) of a first setpoint ($S_1$) for the optical properties of a dentin region, the definition (14) of a second setpoint ($S_2$) for the optical properties of an enamel region, the definition (15) of a third setpoint ($S_3$) for a thickness of the enamel region of the dental prosthesis part (6), the selection and provision (16) of a dental prosthesis mold block (5) having a dentin region made from a material.

15 Claims, 5 Drawing Sheets

(51) Int. Cl.
*A61C 9/00* (2006.01)
*G06F 19/00* (2018.01)
*C09K 3/00* (2006.01)
*B24B 1/00* (2006.01)
*B01D 47/00* (2006.01)
*A61C 5/70* (2017.01)

(58) Field of Classification Search
USPC .............. 700/98; 106/35; 451/28; 264/20; 433/203.1
See application file for complete search history.

(56) References Cited

U.S. PATENT DOCUMENTS

| | | | | |
|---|---|---|---|---|
| 7,013,191 B2* | 3/2006 | Rubbert | ............ | A61C 7/12 433/8 |
| 7,623,942 B2 | 11/2009 | Touchstone | ............ | 700/182 |
| 7,865,261 B2* | 1/2011 | Pfeiffer | ............ | A61C 13/0004 359/458 |
| 8,665,257 B2* | 3/2014 | Ernst | ............ | A61C 13/0004 345/419 |
| 2005/0043837 A1* | 2/2005 | Rubbert | ............ | A61C 7/00 700/98 |
| 2005/0132928 A1* | 6/2005 | Culp | ............ | A61C 13/082 106/35 |
| 2006/0106484 A1* | 5/2006 | Saliger | ............ | A61C 8/0048 700/182 |
| 2006/0122719 A1* | 6/2006 | Kopelman | ............ | A61C 13/0004 700/98 |
| 2006/0147874 A1 | 7/2006 | Touchstone | | |
| 2008/0160485 A1* | 7/2008 | Touchstone | ............ | A61C 13/0004 433/215 |
| 2008/0199826 A1* | 8/2008 | Jia | ............ | A61C 19/10 433/26 |
| 2009/0181346 A1 | 7/2009 | Orth | | |
| 2010/0268363 A1* | 10/2010 | Karim | ............ | A61C 13/0004 700/98 |
| 2010/0285429 A1* | 11/2010 | Karim | ............ | A61C 13/0022 433/199.1 |
| 2011/0104643 A1* | 5/2011 | Giordano | ............ | A61C 13/0022 433/203.1 |
| 2011/0189636 A1 | 8/2011 | Thiel et al. | ............ | 433/199.1 |
| 2011/0212419 A1* | 9/2011 | Schweiger | ............ | A61C 13/0004 433/202.1 |
| 2012/0205828 A1 | 8/2012 | Laubersheimer et al. | | |
| 2014/0356815 A1 | 12/2014 | Spalt et al. | | |

FOREIGN PATENT DOCUMENTS

| | | |
|---|---|---|
| DE | 10 2006 021640 B3 | 10/2007 |
| DE | 10 2011 116 853 A1 | 4/2013 |
| EP | 0 482 000 B1 | 4/1993 |
| EP | 0 850 601 A2 | 7/1998 |
| EP | 2 363 094 A2 | 9/2011 |
| EP | 2 486 892 A1 | 8/2012 |
| WO | 90/13268 A1 | 11/1990 |
| WO | WO 02/09612 A1 | 2/2002 |
| WO | 2006/0734585 A2 | 7/2006 |
| WO | WO 2008/083358 A1 | 7/2008 |
| WO | WO 2008083358 A1 * | 7/2008 ......... A61C 13/0022 |
| WO | WO 2009/070470 A1 | 6/2009 |
| WO | WO 2010/010082 A1 | 1/2010 |
| WO | 2013/060460 A1 | 5/2013 |

OTHER PUBLICATIONS

Opposition to European Patent Application No. 14157753.6, filed Sep. 13, 2016.

* cited by examiner

METHOD AND DEVICE FOR THE PRODUCTION OF A DENTAL PROSTHESIS PART

TECHNICAL FIELD

The present invention relates to a method for the production of a dental prosthesis part. The present invention further relates to a computer program which executes all steps of the method according to the invention when being run on a computer, as well as a data carrier on which said computer program is saved. Finally, the invention relates to a dental CAD/CAM system which is designed to execute the method according to the invention.

PRIOR ART

To a certain extent, human teeth possess natural diversity with regard to their color. Along with individual aspects, genetics, age, dietary habits and smoking play an important role when it comes to the color of a person's teeth. In dentistry, several color charts have been established to describe the color of human teeth. Specifically, the VITA Classic Color and the VITA 3D Master Colors should be mentioned. Every color system available on the market includes color sample teeth which the dentist can use in order to determine the tooth color of the required dental prosthesis directly in the patient's mouth by direct comparison with the adjacent teeth. In addition, a range of devices have been developed in recent years that, among other things, allow the color of the tooth to be determined via spectroscopic analysis of the light reflected by a tooth. Said devices preferably render their measured values in the form of the color system chosen by the user. The dental technician, whose task is to manufacture a suitable dental prosthesis, usually goes by the colors indicated by the dentist, which are determined by the above-mentioned methods. Dental technicians manufacture ceramic restorations by layering ceramic materials which differ with regard to color and opacity. The basis of their work are constructions made of metal or ceramics. Dental technicians achieve the color required by the dentist by means of formulations developed by the manufacturers of said veneering and layering materials. Said formulations essentially describe which kind of layering with which kind of veneering materials must be performed by the dental technician in order to achieve the color desired by the dentist. In addition, dental technicians use their experience and skill to further analyze the shape and appearance of the teeth.

The production of aesthetically pleasing dental prostheses by means of CAD/CAM techniques (computer-assisted design/computer-assisted manufacturing) and prefabricated blanks is rather difficult, particularly in the case of anterior tooth restorations. Although automated CAD/CAM techniques allow for uniform quality and accuracy of fit of dental prosthesis parts at affordable prices, frequently the size and color of the dental prosthesis milled from a mold block needs to be adjusted in order to make them look as much like natural teeth as possible and to correspond with the aesthetic requirements, in particular with regard to their color. For this purpose, multicolored plastic moldings with predefined varying color layers arranged around a core for use in the production of dental prostheses are known from the prior art. Amongst other things, one disadvantage of these moldings results from the fact that for the production of a precisely fitting dental crown on an existing stump, the latter needs to be covered with sufficient dentin material in order to achieve a natural color effect.

CAD/CAM devices use industrially prefabricated blocks. These blocks were initially unicolored and, due to their high translucency, merely created a color effect sufficient for the posterior tooth region due to the so-called chameleon effect. In order to improve their esthetics, the backs of the anterior dental crowns and veneers were colored. Subsequently, multicolored blocks arranged in even layers were developed in order to offer better solutions for the anterior tooth region. Today it is also possible to form the boundary surfaces between individual material layers as curved surfaces. When the dentist, similar to classic color determination, holds a block of the respective colors next to a neighboring tooth in order to determine the necessary color, the color of the finished restoration then frequently will not match the original block color. On the one hand, this effect can be explained by the dependency on the layer thickness of the color of dental ceramics, and on the other hand by the high translucency of the ceramics, which let the dental stump shine through, for instance, and thus lead to distortion of the resulting color.

The object of the present invention is therefore to provide a method for simple and cost-effective variations in size and color for the dental prosthesis part to be manufactured.

DESCRIPTION OF THE INVENTION

The object is achieved by the method according to the invention for the production of a dental prosthesis part. This method comprises the provision of a dataset for a dental prosthesis part for use in a CAD/CAM technique, the provision of reference data for optical properties of different dentin materials and translucent enamel materials for the dental prosthesis part as well as a relationship between said optical properties, desired optical properties of the dental prosthesis part and the dimensions of the dental prosthesis part, the definition of a first setpoint for the optical properties of a dentin region of the dental prosthesis part, the definition of a second setpoint for optical properties of an enamel region the dental prosthesis part, the definition of a third setpoint for the thickness of the enamel region of the dental prosthesis part, the selection and provision of a dental prosthesis mold block having a dentin region made from material with optical properties that correspond with the first setpoint and which has an enamel region made from a translucent material, the optical properties of which correspond with the second setpoint and in which the dentin region is embedded while forming a boundary surface, the boundary surface at least having a first dentin surface and a second dentin surface, the selection of at least one dentin surface and the production of a dental prosthesis part in accordance with the CAD/CAM technique by material ablation from the dental prosthesis mold block, wherein the thickness of the translucent material is reduced in parallel to the selected dentin surface down to the third setpoint. In particular, the selection of the dental prosthesis mold block is made from a predefined range of dental prosthesis molds.

The optical properties of the dentin material preferably comprise different color values. It is further preferable that the optical properties of the translucent material comprise different translucence values. The invention is based on the assumption that merely the directly visible surfaces of a tooth require sufficiently good aesthetics. In the anterior tooth region, this would be labial surfaces; in the posterior tooth region, the occlusal surfaces of the teeth. The other surfaces play a subordinate role in the method according to the invention.

The relationship is preferably a functional relationship and/or an empirical one. It is further preferred that the first setpoint, the second setpoint and the third setpoint be selected depending on the optical properties of teeth, wherein the dental prosthesis part is intended to be placed next to these teeth within a jaw. Account is taken here of the fact that the color of veneering ceramics depends on their layer thickness. In physics, the underlying effect is known as Rayleigh scatter. For the method according to the invention, the layer thickness dependency of the covering enamel material in connection with the color of the inner structures of the dental prosthesis mold can now be considered in order to select a suitable block from the existing range of dental prosthesis mold blocks.

The method according to the invention is used in connection with dental prosthesis mold blocks which have an inner structure and the same properties as natural teeth with regard to shape, color and translucency. These inner structures are covered by another material which resembles the properties natural teeth in terms of color and translucency. In doing so, it is preferable that the material of the dentin region and the material of the enamel region be each selected independently from the group consisting of ceramic materials and acrylates. It is particularly preferable that the dentin region and the enamel region be made from the same material. It is further preferable that the dentin region and the enamel region show different pigmentations. The enamel region modulates the color perception by differently pronounced transparency and particularly thickness. The color effect is, however, primarily the result of the dentin color.

The dentin region is preferably placed on a dentin base surface, which forms the entire base surface of the dental prosthesis mold block.

The dentin surfaces are preferably curved surfaces which form a common intersection area in the proximal direction, and in a particularly preferred manner a common intersection line. It is further preferable that the first dentin surface and the second dentin surface form opposing surfaces of the dentin region. Thus, for instance, two different opposing directions of the dental prosthesis mold block can be optionally used to manufacture an either differently sized or differently colored dental prosthesis part, the resulting labial surfaces preferably being assignable to a incisor and/or canine tooth or the resulting occlusal surfaces preferably being assignable to a posterior tooth. The profile of the first and the second dentin surface has a slightly convex curvature along the entire surface and is tapered towards the neck or the tip of the tooth. The surface facing the gums, i.e. the palatal surface of the thus producible dental prosthesis part, is more or less deeply hollowed out and at least partially overlaps with the dentin region; however, this part is not visible from the outside.

The translucent material is preferably ablated in such a manner that the color of the resulting dental prosthesis part is determined by the chosen dentin surface and the layer thickness of the enamel region. In so doing, the required layer thickness of the enamel region may considerably differ from the anatomical layer thickness of the enamel.

The dental prosthesis part is particularly a crown or a veneer for an anterior tooth or a canine tooth. This particularly accentuates the advantageous optical properties of a dental prosthesis part produced with the method according to the invention. The first setpoint ($S_1$), the second setpoint ($S_2$) and the third setpoint ($S_3$) are in particular only defined with respect to the labial surface of the anterior or canine tooth. As long as suitable dentin shapes are available, the dental prosthesis part manufactured according to the invention may be used anywhere in the jaw, however. If the dental prosthesis part is a crown or a veneer for a posterior tooth, the first setpoint, the second setpoint and the third setpoint are particularly only defined with respect to the occlusal surface of the posterior tooth.

The invention further relates to a computer program which executes all steps of the method according to the invention when it is run on a computer. That way, a dental CAD/CAM system designed to execute the method according to the invention can be obtained by installing a computer program without the need of any structural modifications. According to the invention, the computer program may be stored on a data carrier.

SHORT DESCRIPTION OF THE DRAWINGS

Exemplary embodiments of the invention are illustrated in the drawings and explained further in the following description.

FIG. 1 shoes a flow diagram of a method according to any of the embodiments of the invention.

EXEMPLARY EMBODIMENTS

Figure 1:
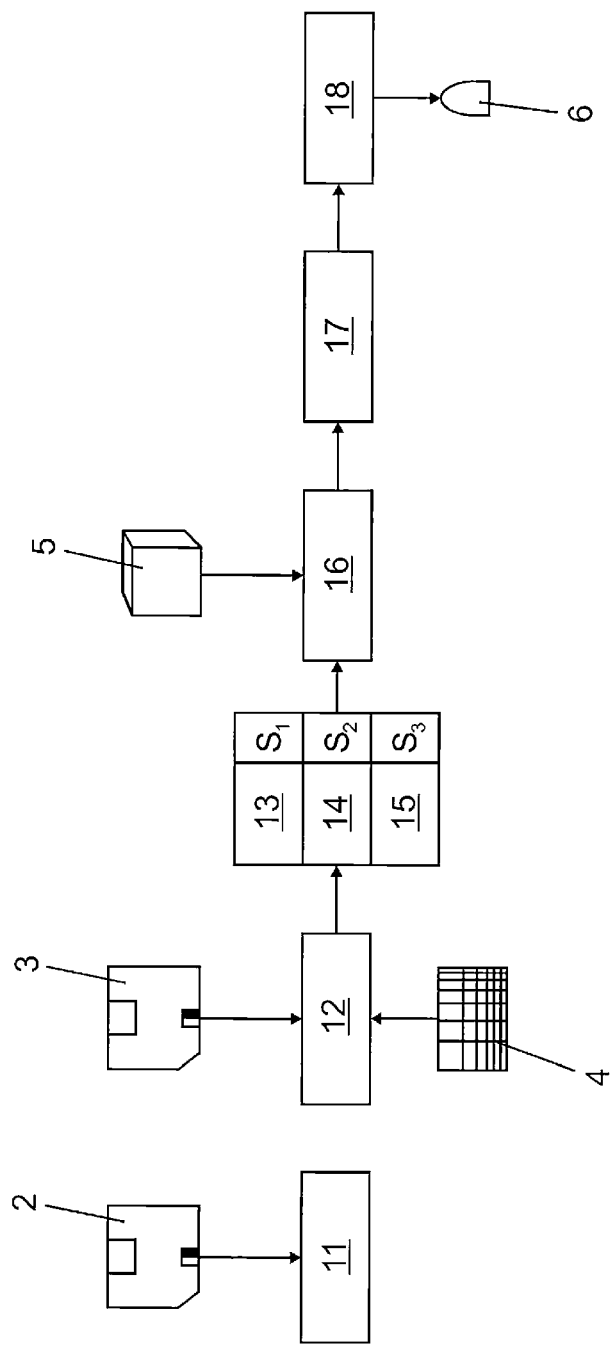

In an exemplary embodiment of the method according to the invention, which sequence is illustrated in FIG. 1, a dataset 2 for a dental prosthesis part 6 to be manufactured is provided for use in a CAD/CAM technique in a first step of the method 11, the dataset having been recorded by a dentist by means of an intraoral camera (e.g. CEREC AC Bluecam or the applicant's Omnicam), for instance. For this purpose, the topographical form of the jaw area to be treated is scanned after having produced a preparation. This can be done immediately and directly, or by means of a positive or negative impression of the respective region. Then the required dental prosthesis part 6 is modeled in the CAD/CAM software by means of known methods. Furthermore, provision 12 is made of reference data 3 for optical properties of various available dentin materials and translucent enamel materials used for the dental prosthesis part 6 as well as a relationship 4 between said optical properties, the desired optical properties of the dental prosthesis part 6 and the dimensions of the dental prosthesis part 6. The reference data 3 are provided by the manufacturer of a dental prosthesis mold block 5. The relationship 4 can be stored in a software program as a functional relationship or an empirical relationship.

The user selects the desired color in which the dental prosthesis part 6 is to be manufactured. In certain circumstances, he might do this for different areas of the visible surfaces. He can define additional features, such as a general opacity of the dental prosthesis part 6, which influence the appearance of the teeth. For that purpose, a first setpoint $S_1$ is made for the optical properties of a dentin region and a definition 14 of a second setpoint $S_2$ for the optical properties of an enamel region of the dental prosthesis part 6 as well as a definition 15 of a third setpoint $S_3$ for the thickness of the enamel region of the dental prosthesis part 6.

Figure 2:
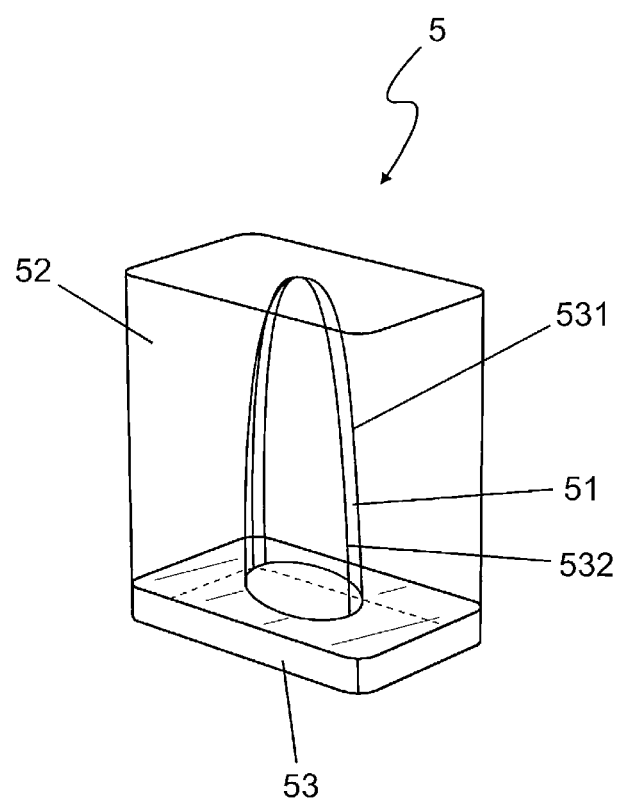
FIG. 2 shows a dental prosthesis mold block which is used for a method according to an embodiment of the invention.

A range of dental prosthesis mold blocks 5 is defined, which inner dentin structure and enamel colors are tailored to the intended application. In doing so, the inner structure is selected with the visible surface that is the most similar to the dental prosthesis part 6 to be produced with regard to size, form and surface curvature. On the basis of the color desired by the dentist, the block which provides the best possible aesthetics from among the range is suggested. Thus, a provision 16 is made of a dental prosthesis mold block 5 as illustrated in FIG. 2. Said mold block comprises a dentin region 51 made from a material with optical properties that correspond with the first setpoint $S_1$. It further comprises an enamel region 52 made from a translucent material with optical properties that correspond with the second setpoint $S_2$ and in which the dentin region 51 is embedded while forming a boundary surface. The dentin region 51 and the enamel region 52 may for instance consist of an identical ceramic material, providing the translucence of the enamel region 52 and an opacity of the dentin region 51 by means of differing pigmentations of these two regions 51, 52. The dentin region 51 is placed on a dentin base surface 54 which forms the entire base surface of the dental prosthesis mold block 5. The boundary surface has at least one first dentin surface 531 and a second dentin surface 532. These dentin surfaces 531, 532 are convex-shaped surfaces which form a common intersection area in the proximal direction. Depending on the desired shape and color of the dental prosthesis part 6 a selection 16 of at least one dentin surface 531, 532 is made. The visible surface of the restoration is tilted toward the dentin surface 531, 532 of the dental prosthesis mold block 5 and moved against it in the parallel or perpendicular direction until the predefined colors are reached as closely as possible. The production 17 of the dental prosthesis part 6 is then performed in accordance with the CAD/CAM technique by ablating the translucent material of the selected dentin surface 531, reducing its thickness down to the third setpoint $S_3$. This is done with a dental CAD/CAM system (e.g. CEREC AC+MC XL by the applicant), which contains an embodiment of the method according to the invention in the form of a computer program.

Figure 3A:
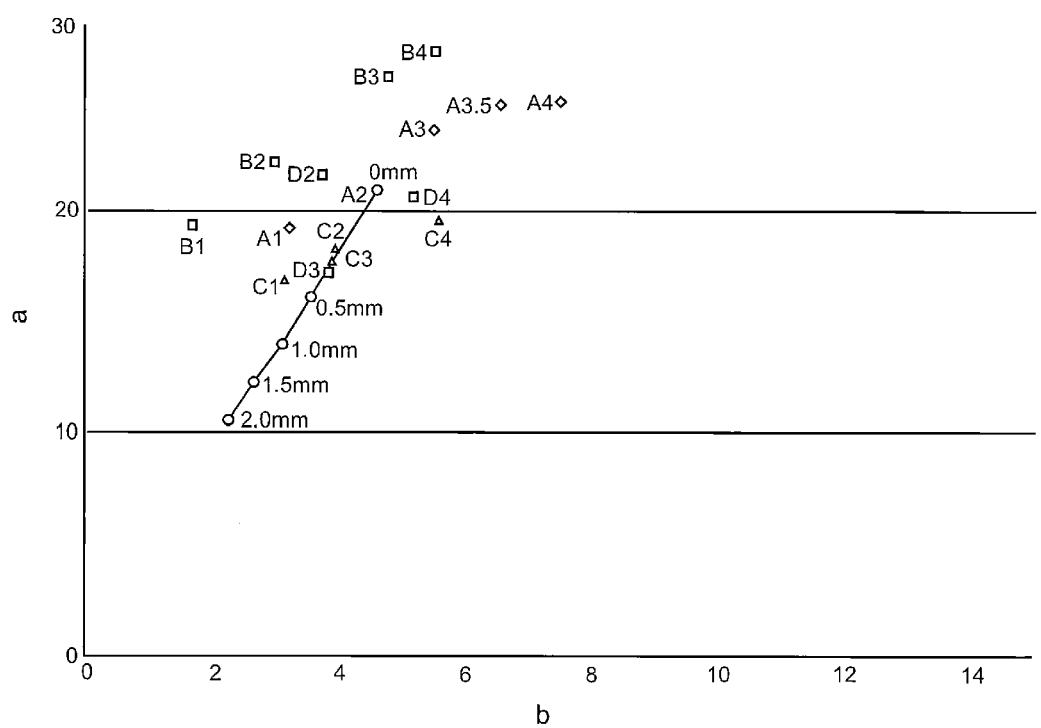
FIG. 3a shows the layer thickness dependence of A2 color values in an a-b diagram in an embodiment of the method according to the invention for the production of dental prosthesis parts.
Figure 3B:
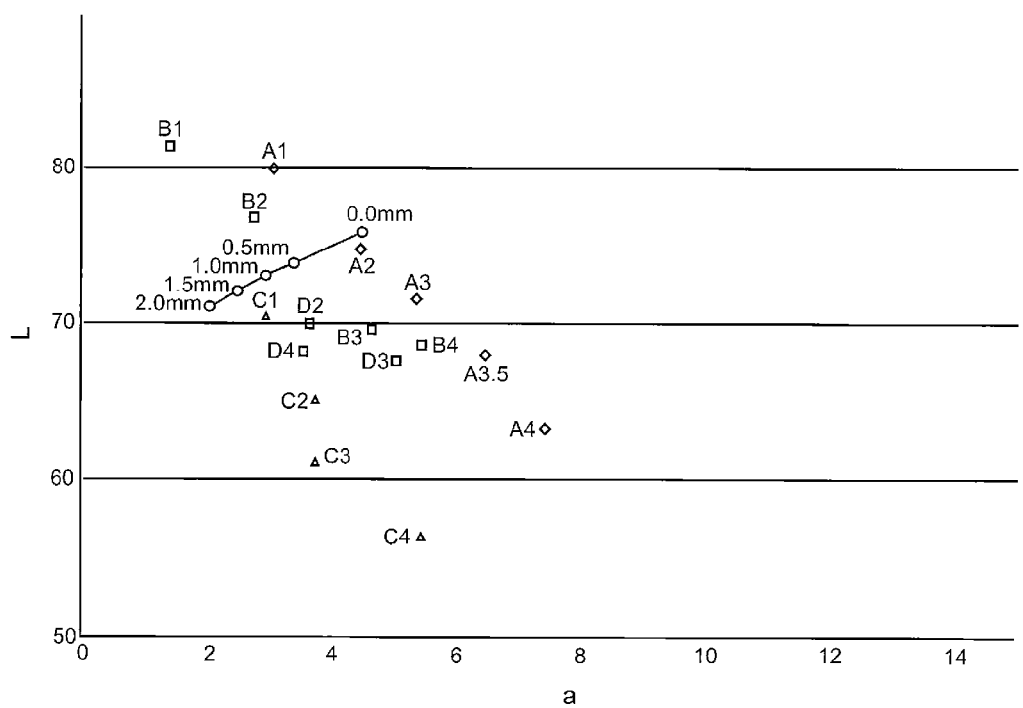
FIG. 3b shows the layer thickness dependence of A2 color values in an a-L diagram in an embodiment of the method according to the invention for the production of dental prosthesis parts.
Figure 3C:
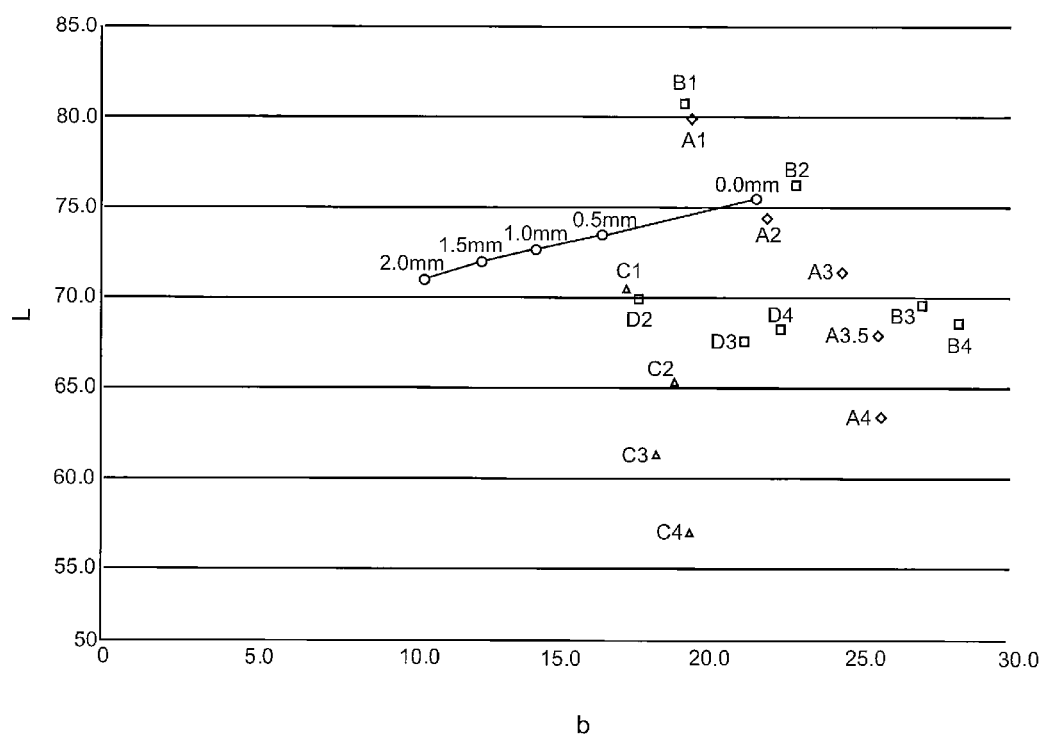
FIG. 3c shows the layer thickness dependence of A2 color values in a b-L diagram in an embodiment of the method according to the invention for the production of dental prosthesis parts.

FIGS. 3*a*-3*c* show which VITA colors can be generated in the Lab color space pursuant to EN ISO 11664-4 with an exemplary dentin core comprising an enamel region 52 with a thickness of 0-2.0 millimeters seen from the viewing direction. FIG. 3*a* shows an a-b section through the Lab color space, FIG. 3*b* shows an a-L section and FIG. 3*c* shows a b-L section. The A2 colors are shown in layer thickness increments of the enamel region of 0.5 millimeters each. A comparison with the positions of the dental colors A1-A4, B1-B4, C1-C4 and D1-D4, which are also shown in FIGS. 3*a*-3*c*, shows that the method according to the invention allows for the production of dental prosthesis parts 6 with colors that resemble those of natural teeth.

The resulting dental prosthesis part 6 may be used as a crown or veneer for an anterior tooth, a canine tooth or a posterior tooth.

The invention claimed is:

1. A method for producing a dental prosthesis, comprising:

receiving a dataset for a dental prosthesis, the dataset including dimensions of the dental prosthesis;

defining: (i) a first setpoint for optical properties of a dentin region of the dental prosthesis, (ii) a second setpoint for optical properties of an enamel region of the dental prosthesis, and (iii) a third setpoint for a thickness of the enamel region of the dental prosthesis;

selecting a dental prosthesis mold block, from a plurality of dental prosthesis mold blocks, the selected dental prosthesis mold block having:
 (i) a dentin region made from a material with optical properties that correspond with the first setpoint,
 (ii) an enamel region made from a translucent material with optical properties that correspond with the second setpoint, and
 (iii) a dentin base surface on which the dentin region is placed,
 wherein the dentin region is bounded by the enamel region and the dentin base surface, and
 wherein a boundary between the dentin region and the enamel region is defined by a first dentin surface and a second dentin surface that are opposing peripheral curved surfaces of the dentin region;

selecting the first dentin surface or the second dentin surface;

positioning a visible surface of the dental prosthesis relative to the selected first or second dentin surface; and producing the dental prosthesis by removing material from the enamel region, wherein the removal of material is done parallel to the selected first or second dentin surface of the selected dental prosthesis mold block down to the third setpoint.

2. The method in accordance with claim 1, wherein the optical properties of the dentin material comprise different color values.

3. The method in accordance with claim 1, wherein the optical properties of the translucent material comprise different translucence values.

4. The method in accordance with claim 1, further comprising:

receiving information corresponding to a relationship between reference data for optical properties of dentin materials and translucent enamel materials that form the plurality of dental prosthesis mold blocks, desired optical properties of the dental prosthesis, and the dimensions of the dental prosthesis, wherein the relationship is a functional relationship or an empirical relationship.

5. The method in accordance with claim 1, wherein the first setpoint, the second setpoint and the third setpoint are dependent on optical properties of a patient's teeth located next to a position for the dental prosthesis.

6. The method in accordance with claim 1, wherein the material of the dentin region and the translucent material of the enamel region are each selected independently from a group comprising ceramic materials and acrylates.

7. The method in accordance with claim 6, wherein the dentin region and the enamel region are made from a same material.

8. The method in accordance with claim 1, wherein the dentin region and the enamel region have a different type of pigmentation.

9. The method in accordance with claim 1, wherein the dentin base surface forms the entire base surface of the dental prosthesis mold block.

10. The method in accordance with claim 1, wherein the first and second dentin surfaces form a common intersection area in a proximal direction.

11. The method in accordance with claim 1, wherein material is removed from the dental prosthesis mold block in such a manner that a color of the dental prosthesis is determined by the selected dentin surface and the thickness of the enamel region.

12. The method in accordance with claim 1,
wherein the dental prosthesis is a crown or a veneer for an anterior or a canine tooth, wherein the first setpoint, and
wherein the second setpoint and the third setpoint are determined with respect to a labial surface of the anterior or the canine tooth.

13. The method in accordance with claim 1,
wherein the dental prosthesis is a crown or a veneer for a posterior tooth, and
wherein the first setpoint, the second setpoint and the third setpoint are determined with respect to an occlusal surface of the posterior tooth.

14. A non-transitory computer readable storage medium storing program instructions configured to cause a computer to execute the method in accordance with claim 1.

15. A dental prosthetic generation system, comprising:
a processor; and
a memory storing at least one control program,
wherein the processor and the memory are operably configured to:
receive a dataset for a dental prosthesis, the dataset including dimensions of the dental prosthesis;
define: (i) a first setpoint for optical properties of a dentin region of the dental prosthesis, (ii) a second setpoint for optical properties of an enamel region of the dental prosthesis, and (iii) a third setpoint for a thickness of the enamel region of the dental prosthesis;
select a dental prosthesis mold block, from a plurality of dental prosthesis mold blocks, the selected dental prosthesis mold block having:
(i) a dentin region made from a material with optical properties that correspond with the first setpoint,
(ii) an enamel region made from a translucent material with optical properties that correspond with the second setpoint, and
(iii) a dentin base surface on which the dentin region is placed,
wherein the dentin region is bounded by the enamel region and the dentin base surface, and
wherein a boundary between the dentin region and the enamel region is defined by a first dentin surface and a second dentin surface that are opposing peripheral curved surfaces of the dentin region;
select the first dentin surface or the second dentin surface;
position a visible surface of the dental prosthesis relative to the selected first or second dentin surface; and
provide instructions for producing the dental prosthesis by removing material from the enamel region, wherein the removal of material is done parallel to the selected first or second dentin surface of the selected dental prosthesis mold block down to the third setpoint.

\* \* \* \* \*